(12) United States Patent
Straub

(10) Patent No.: US 7,008,396 B1
(45) Date of Patent: Mar. 7, 2006

(54) OPHTHALMIC DEVICE AND METHOD OF MANUFACTURE AND USE

(75) Inventor: Howard N. Straub, Aurora, CO (US)

(73) Assignee: Restorvision, Inc., Englewood, CO (US)

( * ) Notice: Subject to any disclaimer, the term of this patent is extended or adjusted under 35 U.S.C. 154(b) by 508 days.

(21) Appl. No.: 09/650,584

(22) Filed: Aug. 30, 2000

Related U.S. Application Data

(60) Provisional application No. 60/152,455, filed on Sep. 3, 1999, provisional application No. 60/178,395, filed on Jan. 27, 2000, provisional application No. 60/206,134, filed on May 22, 2000.

(51) Int. Cl.
*A61M 27/00* (2006.01)

(52) U.S. Cl. ............................................. 604/8

(58) Field of Classification Search ............... 606/161, 606/162, 166, 167, 107, 172; 623/4–5, 905, 623/5.11; 604/8–9
See application file for complete search history.

(56) References Cited

U.S. PATENT DOCUMENTS

| | | | |
|---|---|---|---|
| 4,439,198 A | 3/1984 | Brightman, II et al. | |
| 4,521,210 A * | 6/1985 | Wong | 604/8 |
| 4,549,529 A | 10/1985 | White | |
| 4,863,457 A | 9/1989 | Lee | |
| 4,946,436 A | 8/1990 | Smith | |
| 5,354,331 A | 10/1994 | Schachar | |
| 5,443,505 A | 8/1995 | Wong et al. | |
| 5,465,737 A | 11/1995 | Schachar | |
| 5,489,299 A | 2/1996 | Schachar | |
| 5,503,165 A | 4/1996 | Schachar | |
| 5,520,631 A | 5/1996 | Nordquist | |
| 5,529,076 A | 6/1996 | Schachar | |
| 5,558,630 A | 9/1996 | Fisher | |
| RE35,390 E | 12/1996 | Smith | |
| 5,607,437 A * | 3/1997 | Simon et al. | 606/166 |
| 5,707,643 A | 1/1998 | Ogura et al. | |
| 5,722,952 A | 3/1998 | Schachar | |
| 5,731,909 A | 3/1998 | Schachar | |
| 5,766,242 A | 6/1998 | Wong | |
| 5,774,274 A | 6/1998 | Schachar | |
| 5,824,086 A | 10/1998 | Silvestrini | |
| RE35,974 E | 12/1998 | Davenport | |
| 5,846,256 A | 12/1998 | Mathis | |
| 5,855,604 A | 1/1999 | Lee | |
| 5,876,439 A | 3/1999 | Lee | |
| 5,888,243 A | 3/1999 | Silvestrini | |
| 5,919,228 A | 7/1999 | Hennig | |
| 5,944,752 A | 8/1999 | Silvestrini | |
| 5,964,748 A | 10/1999 | Peyman | |
| 6,007,578 A | 12/1999 | Schachar | |
| 6,228,093 B1 * | 5/2001 | Tomalla | 606/107 |
| 6,673,111 B1 | 1/2004 | Baikoff | 623/4.1 |

(Continued)

FOREIGN PATENT DOCUMENTS

FR    2784287    10/1998

(Continued)

OTHER PUBLICATIONS

Daniele et al., "Gelatin as an Absorbable Implant in Scleral Buckling Procedures," Arch Ophthal, 80:115-119 (1968).

(Continued)

*Primary Examiner*—Vy Q. Bui
(74) *Attorney, Agent, or Firm*—Thomas M. Saunders; Brown Rudnick Berlack Israels LLP

(57) ABSTRACT

A torsion resistant scleral-tensioning stent useful in the correction of presbyopia and further including a method of chronic ocular fluid control utilizing such device.

16 Claims, 15 Drawing Sheets

U.S. PATENT DOCUMENTS

| | | |
|---|---|---|
| 6,682,560 B1 | 1/2004 | Baikoff .................. 623/4.1 |
| 6,692,524 B1 | 2/2004 | Baikoff .................. 623/4.1 |
| 6,712,847 B1 | 3/2004 | Baikoff et al. ........... 623/4.1 |

FOREIGN PATENT DOCUMENTS

| | | |
|---|---|---|
| WO | WO 94/18921 | 2/1993 |
| WO | WO 99/17684 | 10/1997 |
| WO | WO 99/17691 | 10/1997 |
| WO | WO 00/25703 | 11/1998 |

OTHER PUBLICATIONS

Hashizoe et al., "Biodegradable Polymeric Device for Sustained Intravitreal Release of Ganciclovir in Rabbits," Current Eye Research, 112(10):633-639 (1997).

Mathews, "Scleral Expansion Surgery Does Not Restore Accommodation in Human Presbyopia" Opthalmology, 106 (5) 873-877 (1999).

Mathews, "Scleral Expansion Surgery Does Not Restore Accommodation in Human Presbyopia" Opthalmology 1999; 106:873-877(1999), J. Refractive Surgery, Abstracts With Comments by Elander, 15 (1999).

Schachar et al., "In Vivo Increase of the Human Lens Equatorial Diameter During Accommodation," American Journal of Physiology R670-R676 (1996).

Yang et al., "Scleral Expansion: A New Surgical Technique To Correct Presbyopia," Investigative Ophthalmology & Visual Science, Abstract 38(4) 2290 (1997).

Schachar, "Cause and Treatment of presbyopia With a Method for Increasing the Amplitude of Accommodation," Ann Ophthalmol 24:445-452 (1992).

Schachar et al., "Mathematic Proof of Schachar's Hypothesis of Accommodation," Ann Ophthalmol 25:5-9 (1993).

Schachar et al., "Experimental Support for Schachar's Hypothesis of Accommodation," Ann Ophthalmol 25:404-409 (1993).

Schachar et al., "A Physical Model Demonstarting Schachar's Hypothesis of Accommodation," Ann Ophthalmol 26:4-9 (1994).

Schachar, "Zonular Function: A New Hypothesis With Clinical Implications," Ann Ophthalmol 26:36-38 (1994).

Schachar et al., "The Effect of Gravity on the Amplitude of Accommodation," Ann Ophthalmol 26:65-70 (1994).

Schachar et al., "The Mechanism of Accommodation and Presbyopia in the Primate," Ann Ophthalmol 27:58-67 (1995).

Schachar et al., "The Mechanism of Ciliary Muscle Function," Ann Ophthalmol 27:126-132 (1995).

Schachar, "Histology of the Ciliary Muscle-Zonular Connections," Ann Ophthalmol 28:70-79 (1996).

Schachar et al., "Equatorial Diameter During Accommodation," American Physiological Society R670-R676 (1996).

Yee et al., "Scleral Expansion: New Surgical Technique To Correct Presbyopia," Investigative Ophthalmology & Visual Science, vol.30(4), 5 (1997).

Glasser et al., "Presbyopia and the Optical Changes in the Human Cyrstalline Lens with Age," Vision Res., 38:209-229 (1998).

Schachar, "Pathophysiology of Accommodation and Presbyopia," J. Florida M.A. 81:268-271 (1994).

Schachar et al., "A Revolutionary Variable Focus Lens," Annals of Ophthalmology, 2811-18 (1996).

Adler-Grinberg, "Questioning Our Classical Understanding of Accommodation and Presbyopia," Am. J. Optometry & Physiological Optics, 63(7) 571-580 (1986).

Arons, "LASIK and PRK clinical results are hot topics at the RSIG and ISRS meetings," Ocular Surgery News, http://www.slackline.com/eye/osn/199901a/lasik.asp, Jan. 1, 1999.

Atchison, "Accommodation and Presbyopia," Ophthal Physiol. Opt., 15(4):255-272 (1995).

Banuelos et al., "Expandable Silicone Implants for Scleral Buckling," Arch Ophthalmol., 89:500-502 (1973).

Bernatchez et al., "Biocompatibility of a new semisolid bioerodable poly(ortho ester) intended for the ocular delivery of 5-fluorouracil," J. Biomedical Materials Research, 28:1037-1046 (1994).

Billson et al., "Resiting Molteno Implant Tubes," Ophthalmic Surgery and Lasers, 27:801-803 (1996).

Brockhurst. "Dystrop[hic Calcification of Silicone Scleral Buckling Implant Materials," Am J. Ophthalmol, 115:524-529 (1993).

Brouillette et al., "Long-term results of modified trabeculectomy with Supramid implant for neovascular glaucoma," Can. J. ophthalmol, 22(5):254-256 (1987).

Cameron et al., "Clinico-histopathologic Correlation of a Successful Glaucoma Pump-shunt Implant," Ophthalmology, 95:1189-1194 (1988).

Campbell et al., "Fluctuations of Accommodation under Steady Viewing Conditions," J. Physiol., 145:579-594 (1959).

Coleman et al., "Initial Clinical Experience with the Ahmed Glaucoma Implant," Am. J. Ophth, 120:23-31 (1995).

Coleman et al., "Clinical Experience with the Ahmed Glaucoma Valve Implant in Eyes with prior or Current Penetrating Keratoplasties," Am. J. Ophth, 123:54-61 (1997).

Colosi et al, "Intrusion of Scleral Implant Associated with Conjunctival Epithelial Ingrowth," Am.J. Ophthalmol, 83: 504-507 (1977).

Coltair et al., "Scleral pocket incision applied to insertion of the nut and bolt keratoprosthesis," J. Cataract Refract Surg, 16:649-651 (1990).

Crucea et al, "[Artificial drainage devices in glaucoma]" Oftalmologia, 47(2):5-10 abstract only.

Daniele et al. "Gelatin as an Absorbable Implant in Scleral Buckling procedured," Arch Ophthal, 80:115-119 (1968).

Ellis, "Surgical Conquest of presbyopia; Are There Implications for Cataract and Glaucoma" Refractive Surgery, 38-44 (1999).

El-Sayyad, "The Use of Releasable Sutures in Molteno Glaucoma Implants to Reduce Postoperative Hypotony," Ophthalmic Surgery, 22:82-84 (1991).

Girard et al., "Scleral fixation of a subluxated posterior chamber intraocular lens," J Cataract Refract Surg, 14:326-327 (1988).

Hashizoe et al, "Implantable biodegradable polymeric device in the treatment of experimental proliferative vitreoretinopathy," Curr Eye Res 14(6):473-477 (1995).

Hashizoe et al, "Scleral plug of biodegradable polymers for controlled drug release in the vitreous," Arch Ophthalmol 112(10):1380-1384 (1994).

Hashizoe et al, "Biodegradable polymeric devices for sustained intravitreal release of glanciclovir in rabbits," Current Eye Research 112(10):633-639 (1997).

Hasty et al, "Primate Trabeculectomies with 5-fluorouracil Collagen Implants," Am J Ophthalmol 109:721-725 (1990).

Hilton et al., "The Removal of Scleral Buckles," *Arch Ophthalmol*, 96:2061-2063 (1978).
Ho et al, "The MAI hydrophilic implant for scleral buckling: a review." *Ophthalmic Surg.* (6):511-5 (1984).
Jacklin et al, "Gelatin as an Absorbable Implant in Scleral Buckling Procedure," *Arch Ophthalmol*, 79:286-289 (1968).
Jacob et al., "Synthetic scleral reinforcement materials. II Collagen types in the fibrous capsule," *J. Biomedical Materials Research*, 32:181-186 (1966).
Krupin et al, "Filtering Valve Implant Surgery for Eyes with Neovascular Glaucoma," *Am J Ophthalmol*, 89:338-343 (1980).
Krupin et al, "Long-Term Results of Valve Implants in Filtering Surgery Eyes with Neovascular Glaucoma," *Am J Ophthalmol*, 95:775-782 (1983).
Krupin et al, "A Long Krupin-Denver Valve Implant Attached to a 180° Scleral Explant for Glaucoma Surgery," *Ophthalmol*, 95:1174-1180 (1988).
Kimura et al., "A new Vitreal Drug Delivery System Using an Implantable Biodegradable Polymeric Device," *Investigative Ophthalmol and Visual Science*, 35:2815-2819 (1994).
King et al., "Gelatin Implants in Scleral Buckling Procedures," *Arch Ophthalmol*, 93:807-811 (1975).
Lambert et al., "Wedge Implant Used as an Explant," *Am J Ophthalmol*, 101:488-489 (1986).
Lamberts et al., "A New Alloplastic Materials for Ophthalmic Surgery," *Ophthalmic Surgery*. 9:35-42 (1978).
Law et al., "Retinal Complications after Aqueous Shunt Surgical Procedures for Glaucoma," *Arch Ophthalmol*, 114: 1473-1480 (1996).
Levit et al., "Use of Ophthalmic Gelfilm in retinal Surgery," *Ann Ophthalmol*, 1613-1616 (Dec. 1975).
Lipner, "A Closer Look at Scleral Surgery," Eyeworld, (Sep. 13, 1999) http://www.eyeworld.org/sep99/999p34.asp.
Lincoff et al., "The Changing Character of the Infected Scleral Implant," *Arch Ophthalmol*, 84:421 et seq, (1970) [Partial copy, full text to follow].
Liu et al., Scleral Buckling with a Soft Xerogel Implant: II Experiments In Vivo, *Ophthalmic Surgery*, 10:52-56 (1979).
Lloyd et al., "Initial Clinical Experience with Baerveldt Implant in Complicated Glaucomas," *Ophthalmology*, 101: 650-640 (1994).
Luttrull et al., "Pars Plana Implant and Vitrectomy for Treatment of Neovascular Glaucoma," *Retina*, 16:379-387 (1995).
Luttrull et al., "Initial Experience with Pneumatically Stented baerveldt implant modified for Pars Plana Insertion in Complicated Glaucom" *Ophthalmology*, 107:143-149 (2000) [Abstract only].
Marin et al., "Long-term Complications of the MAI Hydrogel Intrascleral Buckling Implant," *Arch Ophthalmol*, 110:86-88 (1992).
Mathews et al., Scleral Expansion Surgery Does Not Restore Accommodation in Human Presbyopia, *Ophthalmology*, 106: 873-877 (1999).
Melamed et al., "Molteno Implant Surgery in refractory Glaucoma," *Survey of Ophthalmology*, 34:441-448 (1990).
Minckler et al., Clinical Experience with the Single-plate Molteno Implant in Complicated Glaucomas, *Ophthalmology* 95:1181-1188 (1988).
Miyamoto et al, "Biodegradable scleral implany for controlled release of flocanazole," *Current Eye Research*, 16:930-935 (1997).

*Ocular Surgery News*, "Presbyopia reversible in Pilot Studies," Jul. 1, 1999; http://www.slackinc.com/eye/osn/199907a/presby.asp.
Peiffer et al., "Long-term Comparative Study of the Schochet and Joseph Glaucoma Tube Shunts in Monkeys," *Ophthalmic Surgery*, 21:55-59 (1990).
Pruett, "The Fishmouth Phenomenon," *Arch Ophthalmol*, 95:1777-181 (1977).
Rabowsky et al., "The Use of bioerodeable polymers and daunarubicin in glaucoma filtration surgery," *Ophthalmology*, 103:800-807 (1996).
Ray et al., "Gelatin Implants in Scleral Buckling Procedures, " *Arch Ophthalmol*, 93:799-802 (1975).
Refojo, "Polymers in Ophthalmic Surgery," *J.Biomed. Mater.Res.*, 5:113-119 (1971).
Refojo et al., "Experimental Scleral Buckling with a Soft Xerogel Implant," *Ophthalmic Surgery*, 9:43-50 (1978).
Riggs et al., "Intraocular silicone prostheses in a dog and a horse with corneal lacerations," *J. Am. Vet. Med. Assoc.*, 196:617-619 (1990).
Rohr et al., "Surgical Correction f Presbyopia," *J. Osteopathic College of Ophthalmology and Otorhinolaryngology*, 12:34-36 (2000).
Rubsamen et al., "Prevention of Experimental Proliferative Vitreoretinopathy with a Biodegradable Intravitreal Implant for the Sustained Release of Fluoroacil," *Arch Ophthalmol*, 112:407-413 (1994).
Sakamoto et al., "Silicone Sponge Implant in Combination with Episcleral Implant for Retinal Surgery," *Ophthalmic Surgery*, 11:712-718 (1980).
Sarkies et al., "Silicone Tube and Gutter in Advanced Glaucoma," *Trans. ophthalmol. Soc. U.K.*, 144:133-136 (1985).
Schepens et al., "Scleral Implants: An Historic Perspective," *Survey of Ophthalmology*, 35:447-453 (1991).
Sherwood et al., "Prevention of early hypotony associated with Molteno implant new occluding stent technique," *Ophthalmology*, 100:85-90 (1993).
Sherwood et al., "Surgery for Refractory Glaucoma," *Arch Ophthalmol*, 105:562-569 (1987).
Sidoti et al., "Epithelial Ingrowth and Glaucoma Drainage Implants," *Ophthalmol*, 101:872-875 (1994).
Sidoti et al., "Aqueous Tube Shunt to a Pre-existing Episcleral Encircling Element in the Treatment of Complicated Glaucomas," *Ophthalmol*, 101:1036-1043 (1994).
Smith et al., "One-year results of the intrascleral glaucoma implant," *J Cataract Refract Surg*, 21:453-456 (1995).
Smith et al., "Comparison of the Double-Plate Molteno Drainage Implant with the Schochet Procedure," *Arch Ophthalmol*, 110:1246-1250 (1992).
Speigel et al., "Anterior Chamber Tube Shunt to an Encircling Band (Schochet procedure) in the Treatment of Refractory Glaucoma," *Ophthalmic Surgery*, 12:804-807 (1992).
Strubble et al. "In vitro low characteristics of the Amhed and self-constructed anterior chamber shunts," *Am.J.Vet.Res* 58: 1332-1337 (1997).
Sveinsson et al., "Trabeulectomy and gelatin implants," *Acta Ophthalmologica*, 70:645-650 (1992).
Susanna, "Modifications of the Molteno Implants and implant Procedure," *Ophthalmic Surgery*, 22:611-613 (1991).

Szymañski, "Scleral free auto-implant plug with mitomycin as limitation of trepanosclerectomy flow in glaucoma filtering surgery," *International Ophthalmology*, 20:89-94 (1997).

Tanji et al., Fascia Lata Patch Graft in Glaucoma Tube Surgery, *Ophthalmology*, 103:1309-1312 (1996).

Tawakol et al., "Gore-Tex™ Soft Tissue Bands as Scleral Explants in Rabbits: A Preliminary Histologic Study," *Ophthalmic Surgery*, 20:199-201 (1989).

Watzke, "Scleral Patch Graft for Exposed Episcleral Implants," *Arch Ophthalmol*, 102:114-115 (1984).

Wilson, "New hope for presbyopia: PMMA scleral bands show promise," *Eyeworld*, (1999) http://www.;eyeworld.org/apr98/963.html.

Wilson et al., "Aqueous Shunts—Molteni versus Schocket," *Ophthalmology*, 99:672-678 (1992).

Wilson-Holt et al.,"Hypertrophy floowing insertion of inferiorly sited double-plate Molteno tubes," *Eye*, (Pt 5)515-20 (1992) [Abstract only].

Yoshizumi, "Exposure of Intrascleral Implants." *Ophthalmology*, 87:1150-1154 (1980).

Yoshizumi, "Erosion of Implants in Retinal Detachment Surgery" *Annals of Ophthalmology*, 87:430-434 (1983).

* cited by examiner

"STABLE"

"UNSTABLE"

"CRITICAL POINT"

EFFECTIVE WIDTH OF A ROUNDED BOTTOM STENT

OPHTHALMIC DEVICE AND METHOD OF MANUFACTURE AND USE

This application claims the benefit under 35 U.S.C. Section 119(e) of provisional application 60/152,455 filed Sep. 3, 1999, 60/178,395 filed Jan. 27, 2000 and 60/206,134 filed May 22, 2000.

FIELD OF THE INVENTION

This invention relates to presbyopia and in particular, it relates to a torsion- resistant scleral-tensioning device and further including a method of chronic ocular fluid control utilizing such device.

BACKGROUND OF THE INVENTION

Without being bound by any particular theory, recent studies in ophthalmology suggest that presbyopia that arises almost universally among people in their 40s is the result of the continued growth of the lens. Lens growth results in shortening the length between the lens and ciliary muscles. This compromises the ability of the ciliary muscles to effectively stretch the lens. This is exhibited as a reduced amplitude of accommodation. Increasing the effective working distance between the ciliary muscles and the lens equator is effected by increasing the diameter of the sclera in the region of the ciliary body. This theory is not confirmed and other or additional factors may obtain.

Astigmatism is another prevalent visual problem. Astigmatism occurs when light entering the eye is "split" into two separate parts instead of focusing to one, precise point on the retina. Astigmatism usually occurs because of a corneal irregularity. Historically, a lens with two different power curves (toric lens) has been employed to correct astigmatism. In practice, these lenses have a variable edge profile that is thinner in some places and thicker in others. Some amounts of astigmatism are corrected surgically in patients with astigmatism alone or astigmatism present with nearsightedness. There is no present procedure to correct astigmatism combined with farsightedness.

The cornea accounts for about 70% of the eye's focusing power. By altering the shape and power of the cornea, the optical characteristics of the eye can be changed. This is the basis for most refractive surgical procedures.

In the practice of this invention, astigmatism (with or without near or farsightedness) is ameliorated by placement of stents proximate to but not in the corneal visual pathway.

The sclera is an element of the fibrous tunic of the eye (along with the cornea). The sclera ranges from about 0.13 to 1 mm in thickness. The tendons of the eye muscles insert on the sclera.

SUMMARY OF THE INVENTION

This invention comprises a torsion resistant scleral-tensioning stent for positioning in a tunnel formed intrasclerally in a globe of an eye, comprising a generally t-shaped body as seen in the intersection arms and having a cross portion (proximal end) with a bottom surface which is optionally flat in some embodiments and a leg portion extending substantially perpendicularly from a side surface of said cross portion, the leg portion having a bottom surface with an arcuate portion and a substantially planar portion at an end of the leg portion distal from said cross portion (distal end), wherein the arcuate portion has a curvature greater than a radius of curvature of the globe of the eye in the area of the tunnel, whereby at least a portion of the arcuate bottom surface is adapted to increase the diameter of the scleral size adjacent to the tunnel when the stent is positioned in the tunnel; and wherein the bottom surface of the cross portion is dimensioned to be disposed external to the tunnel for resisting torsional forces on the leg portion. In some embodiments the cross portion extends beyond the tunnel. In particular embodiments the arcuate stent has a base curve of from about 8 to about 9 mm, and optionally a peak of about 7 mm. Particular stents are out-gassing free, and reference is made to stents of thermosetting PMMA.

In some embodiments the stent slopes sharply from a maximum height at the leg-portion to a minimum thickness at the cross portion.

Particular embodiments of the stent are arcuate biased, and optionally in these embodiments a linear bore hole extends from the flange through the body of the stent, with the stent provided with a removable stylet positioned within the bore hole.

In specific embodiments a separate element comprises an anti-torsion-cap adapted and configured to conform to the distal end of said stent.

In some embodiments the distal end of the stent comprises an insertion blade, which is optionally removable.

Some stents of the present invention further comprising affixation means notches.

An aspect of the present invention is a torsion resistant scleral-tensioning multi-arcuate-stent comprising at least about four torsion resistant scleral-tensioning stents positioned about equidistant about the sclera, and in non-circulatory-compression arcs.

This invention includes a method of chronically increasing ocular fluid drainage by the steps of placing at least two torsion resistant scleral-tensioning arcuate-stents and preferably at least about four torsion resistant scleral-tensioning stents positioned about equidistant about the sclera, and in non-circulatory-compression arcs.

This invention also includes a method of chronically reducing ocular fluid out-flow resistance by the steps of placing at least two torsion resistant scleral-tensioning arcuate-stents and preferably at least about four torsion resistant scleral-tensioning stents positioned about equidistant about the sclera, and in non-circulatory-compression arcs.

This invention additionally includes a method of chronic glaucoma palliation by the steps of placing at least two torsion resistant scleral-tensioning arcuate-stents and preferably at least about four torsion resistant scleral-tensioning stents positioned about equidistant about the sclera, and in non-circulatory-compression arcs. Glaucoma, ocular hypertension, and particularly open angle glaucoma are controlled by increasing frequency and maximum excursion of lens movement by increasing amplitude of lens shape change in daily use. Without being bound by any particular theory it is believed that opening the canal of Schlemm is palliative of glaucoma.

A noted embodiment of the invention is a method of presbyopia palliation by the steps of placing at least two torsion resistant scleral-tensioning arcuate-stents and preferably at least about four torsion resistant scleral-tensioning stents positioned about equidistant about the sclera, and in non-circulatory-compression arcs.

An additional embodiment of the invention comprises a method of avoiding, delaying, or reversing the lens opacification by the method of placing at least two and preferably four scleral-tensioning arcuate-stents positioned
 (i) about equidistant about the sclera, and
 (ii) in non-circulatory-compression arcs.

A yet further embodiment of the invention comprises a method of astigmatism reduction by the steps of placing at least one torsion resistant scleral-tensioning arcuate-stent in an intra-scleral position proximate to the lens and beyond the visual pathway to advance the outward surface of a lens in the quadrant nearest the stent.

DETAILED DESCRIPTION OF THE INVENTION

Definitions

A. Stents of this invention are dimensioned from about 2 mm to about 6 mm, in length with particular reference to about 4.75 to about 5 mm. In particular embodiments the stents are tapered from the sides with a narrow end of about 550 microns to about 650 microns and a wide end of about 600 to about 850 microns adjoining a flange of about 1000 to about 15 hundred microns with particular reference to about 1200 microns. Stents with the long axis generally describing an arc are noted with a radii at the upper surface of from about 3 to about 10 mm with particular reference to about 4.0 to about 4.7 mm and particularly about 4.4 mm. Stents with the long axis generally describing an arc are noted with a radii at the lower surface of from about 3 to about 15 mm with particular reference to about 7 to about 10 mm and particularly about 8.8 mm.

B. Scleral-tensioning as to a stent shall mean a support structure that elevates or "tents" the sclera thus expanding the globe. Scleral-tensioning increases lens zonule tensioning.

C. Arcuate as to a stent shall mean substantially all weight bearing contact inward to the sclera is borne at the ends of the stent. While arcuate applies to stents comprising an arc as a segment of circle, arcuate shall be broadly construed to include any structure that provides for substantially all weight bearing contact inward to the sclera is borne at the ends of the stent. In one embodiment the radius of the curvature is from about 9.5 to 8 mm and particularly about 9 mm and 8.8 mm. In one stent the top surface is about 5 mm at the ends rising to about 9 mm at the center.

D. Presbyopically-effective scleral tensioning is achieved when the total tenting is from about 250 mm and further at least about 400, and particularly about 500 to about 700 mm or more. Lesser amounts of tenting can be effective.

E. Efflux-effective tensioning shall mean total tenting from about 200 mm, but further includes 250 mm and further at least about 400, and particularly about 500 to about 700 mm or more. Efflux-effective tensioning is useful in controlling pressure buildup in the anterior chamber of the eye associated with glaucoma. Chronic open angle glaucoma is characterized at intra ocular pressures above about 20 to 24 mm Hg. Controlled glaucoma is about 20 and preferable 16 mm Hg or less. It is noted that even low tension glaucoma is treated by the present invention reducing intra ocular pressures from about 14 to 20 mm Hg to about 10 mm Hg.

F. Torsion-resistance is provided by mechanical means such as a flange and with an optional flat foot rather than a round bottom stent. Torsion resisting structural features are broadly termed torsion resistance elements.

Figure 1A:
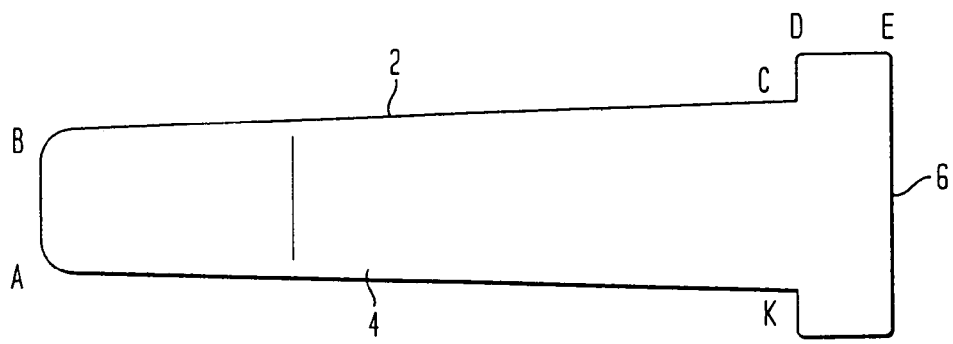
FIG. 1(a) is a top plan view of a scleral stent, one embodiment, of the present invention.
Figure 9A:
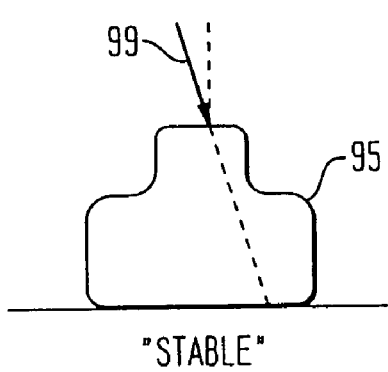
FIGS. 9(a)–9(c) are rear elevational views of the stent of the invention with force lines showing on-axis and off-axis loading.
Figure 9B:
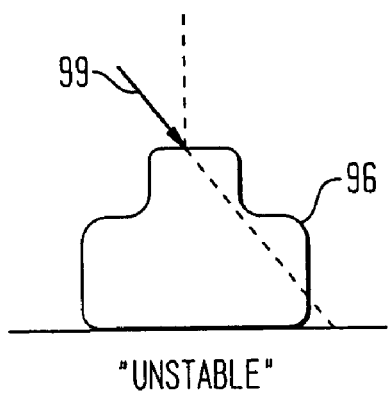
Figure 9C:
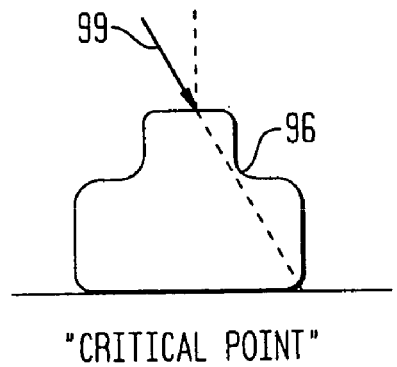

Referring now to FIG. 9 which is a rear view of a stent of the invention similar to that of FIG. 1(a). Orientational stability as seen through flange (96) is resistance to off-axis forces (99) as the sclera adjusts, moves, or deforms. Ignoring slippage, compression, and wedging effects, the stent will tend to rotate about its longitudinal axis when the axis of the net force does not pass through the base of the stent. (FIG. 9(b).) There is a critical angle running through a point ($\alpha$) for any applied net-load beyond which the stent will tend to be unstable. In this respect, refer to (FIG. 9(c). The maximum stent height, the length, the radius of curvature, the height of the flange, and the width of the flange determine this critical angle.

In an embodiment of the present invention substantially as shown in FIG. 1(a) with a length of 5000$\mu$, a radius curve of 8800$\mu$, and height of flange of 500$\mu$ and given a flange width of 1200 microns the orientation-stability on off-axis load is about 35°. The same stent with no flange possesses a far diminished orientation-stability of about 20° off-axis loading. The same stent with a rounded bottom has orientation-stability of about 10° off-axis loading.

Figure 10:
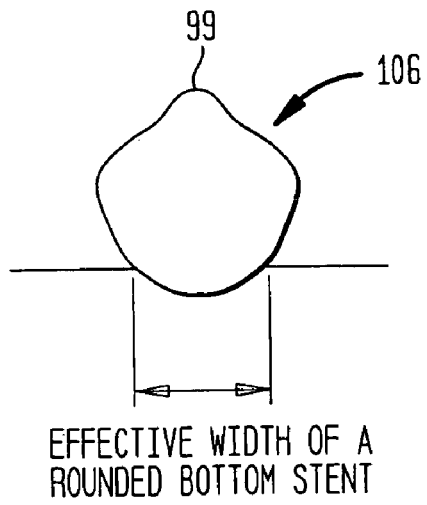
FIG. 10 is a rear elevational view of a non-torsion resistant stent of the prior art illustrating application of forces.

FIG. 10 is a rear view of a round bottom unflanged stent (106). Off-axis forces are indicated by an arrow (99). Therefore, torsion-resistance of the present invention particularly notes a factor superiority of about 1.8 over no-flange unaffixed stents and about 3.5 over rounded bottom unaffixed stents.

If the stent height is increased, for example to provide more tenting, maintaining equivalent stability is optionally achieved by increasing the width of the base by a proportionate amount in order to maintain a given orientation-stability.

Consider an embodiment with a flange width of 1200 microns, and a total height (from the arc length plus the flange height) of 862 microns. To increase tenting another 100 microns and maintain the same orientation-stability the flange width is increased to 1339 microns. That is, the ratio of Flange Width to maximum height is held constant (e.g. 1200/862 and 1339/962).

Other means of maintaining torsion resistance include biocompatible adhesives and mechanical fasteners such as staples and sutures.

Figure 8:
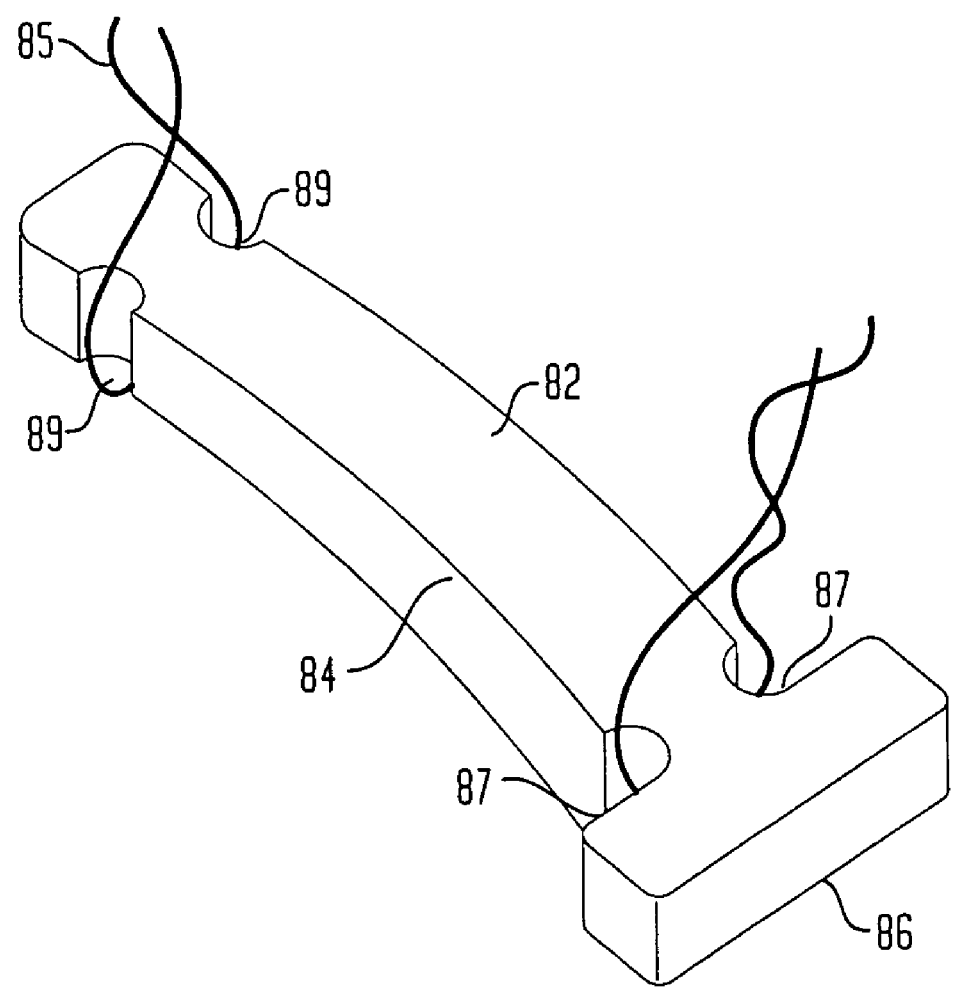
FIG. 8 is a semi-perspective view of a modified stent having a suture placement arrangement.

In some embodiments sutures are be applied, particularly at the extremes of the wide footprint, so as to avoid slipping. In the embodiment of FIG. 8, sutures are applied to maintain contact of the flange to the sclera. When sutured, the bottom of the wide flange will tend to support the on-axis component of the net load and the sutures will only have to support any cross-axis component of force. Only if the net-force is applied beyond the critical angle is it necessary for sutures to support any off-axis component of the load to prevent rotation. A wide flange will tend to reduce the force exerted on the sutures.

Figure 11:
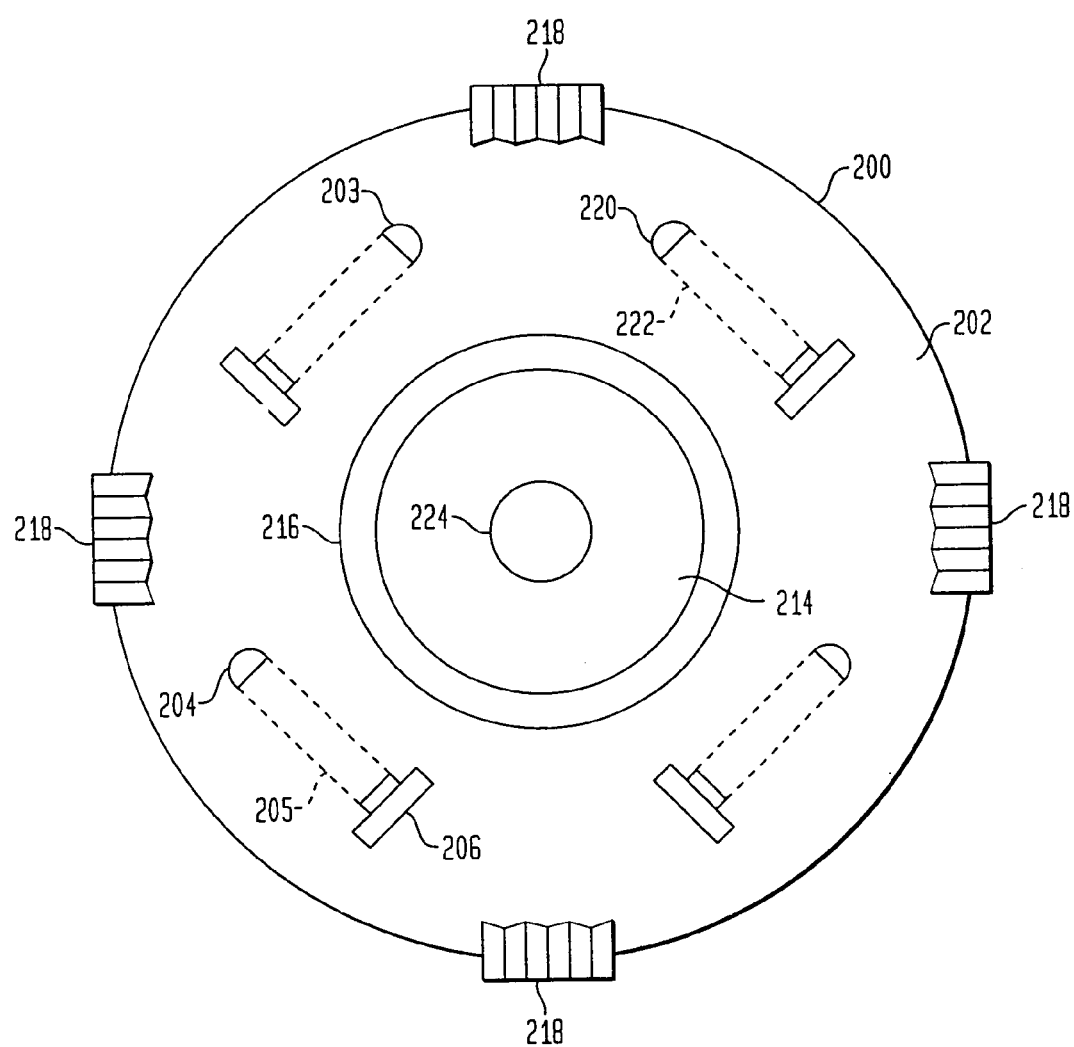
FIG. 11 is a front elevational view of the ocular globe showing location of the stents.

FIG. 11 is a view of the ocular globe (200) with intrasclerally implanted devices. The outer layer of the eye is the sclera (202) and the external muscles (218). The cornea (214) is the most anterior structure with the pupil (224) seen behind and central thereto. The limbus (216) is the junction of sclera (202) and cornea (214). Tunnels (220) in the sclera are seen with anterior margins (222) about 4 to 5 millimeters posterior to the limbus (216). Each tunnel (220) contains the stent having the front end (204) protruding from one end thereof and a flange (206) protruding from the other end. The body (205) of the stent positioned within the tunnel is shown in phantom. The stent is oriented with its protruding front end (207) (204) and flange (206) resting on the sclera and its arcuate peak within the tunnel.

In particular embodiments the torsion-resistant flange of this invention is chronically stable, maintaining maximal tenting for at least about one year, and preferable for about 8 years and in particular embodiments for in excess of 10 years.

Stents of the present invention can be fashioned of any suitable material with attention to bio-compatibility. For example poly-methyl methacrylate ("PMMA"), both thermoset and thermoplastic, are suitable. PMMA is supplied by a number of sources. Thermosetting PMMA is available as Perspex CQ (ICI Derby, England). Thermosetting PMMA is preferred over thermoplastic PMMA because it is outgassing free. That is, it does not release monomers in situ. Teflon® and tantalum are also noted. It is also possible to coat stents with bio-compatible materials if elements of the stent are not bio-compatible. In some embodiments the stent materials contain pigments or dyes. In particular embodiments stents are coated or impregnated with bioactive substances including anti-inflammatory agents/immunomodulating agents and antiinfective agents. Particular stents will contain radio-opaque, radioactive, fluorescent, NMR contrast or other "reporter" materials. Smooth stents with no more than 100 Å peak to valley are noted. A particular advantage of such a smooth surface is the reduction of implant erosion into or out of the sclera. In particular embodiments textured stents are useful permitting adhesion with associated tissues.

Preferably, placement of the stents is adjusted to avoid compression of the ciliary arteries. Placement is preferred at about the 2:00, 4:00, 8:00 and 10:00 positions around the globe. Such placement comprises non-circulatory-compression arcs. Placement compressing the ciliary arteries can be detected by occurrence of anterior segment ischemia. For stent elements overlying ciliary arteries, compression of ciliary arteries is minimized by increased surface area of portions of the stent pressing inward on the eye. In some embodiments it is useful to place stents anywhere from about 3 to about 8 mm and preferably about 4 to 6 mm posterior to the limbus in the oblique quadrants of the eye at a depth of about 250 to 300 microns within scleral tunnels that are about 3 to 5 mm long and preferably about 3.8 to 4.0 mm long.

Referring now to FIGS. 1(a)–1(d), which illustrate one embodiment of the scleral tensioning stent of the invention. A torsion resistant scleral-tensioning stent 2 of the invention is adapted for positioning in a tunnel formed in a sclera of an eye. The stent (2) comprises a generally T-shaped body having a torsion-resistant element, a flange or a cross portion (6) formed with a substantially flat rear bottom surface (10) and a leg portion (4) extending outwardly from a side surface of the portion and having a substantially flat front bottom surface (8). The leg portion (4) is formed with a bottom area having an arcuate region (7) which extends rearwardly from the front bottom surface (8) so that its rear end is situated in the close vicinity to the cross-portion (6). A curvature of the arcuate region (7) is greater than the curvature of the globe in an area of the tunnel. Thus, at least a portion of the arcuate region (7) is adapted to increase the diameter of the scleral size adjacent the tunnel when the stent is positioned within the tunnel. Upon proper positioning of the stent of the invention, the rear bottom surface (10) of the cross portion (6) is adapted to be disposed externally to the tunnel for resisting torsional forces on the leg portion.

As best illustrated in FIGS. 1 (a) and 1 (b), the stent (2) in general and a top area thereof in particular are formed with a front tapered region (12) and a rear tapered region (14). The front tapered region 12 extends rearwardly from a rounded front tip (16) of the leg portion (4) and is provided to facilitate insertion of the stent into the tunnel during the surgery. The rear tapered region (14) slopes downwardly from an area in the vicinity of the junction between the cross portion (6) and the leg portion (4) toward the rear end of the stent.

Figure 2A:
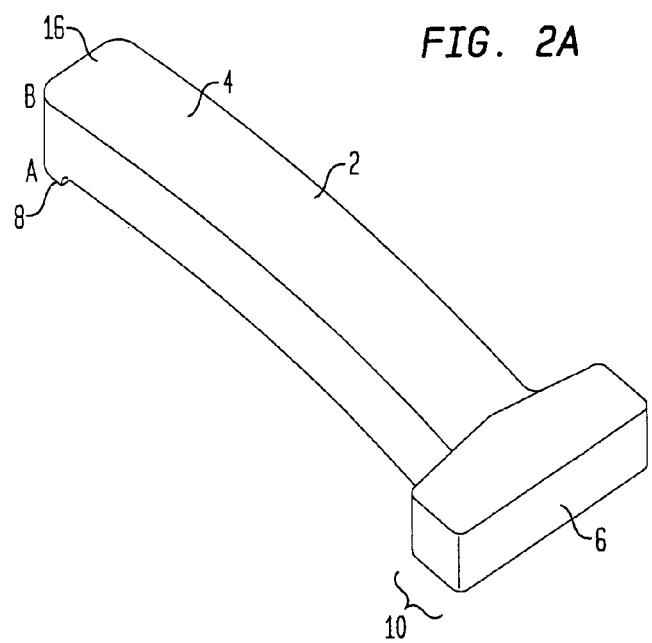
FIG. 2 is a semi-perspective view of a modified embodiment of the scleral stent of FIG. 1(a) having reduced taper in the top to bottom direction at the rear end thereof.

FIG. 2. is a perspective view of the scleral stent (2) of FIG. 1(a). The leg portion (4) of the stent is tapered at the front end (16). The torsion-resistant element or flange (6) is about 1200 microns in width, whereas the length of the portion (10) is about 500 microns. The length of the front torsion-resistant element (8) is about 500 microns.

Figure 3A:
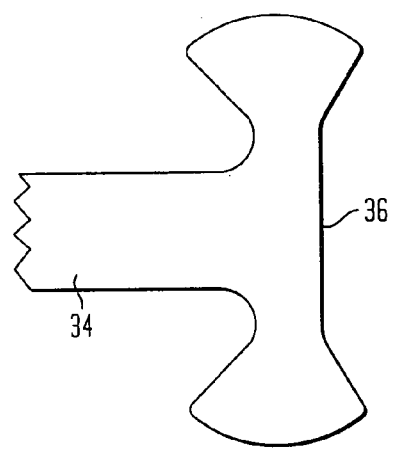
FIG. 3(a) is a top plan view of a modified stent flange.

FIG. 3(a) represents a top partial view of another embodiment of a scleral stent of the present invention. A partially shown leg portion (34) is connected to the cross-member or flange (36) having configuration resembling a butterfly. It is clear from FIG. 3 (a), that parts of the flange (36), situated in the vicinity of the leg portion (34) are substantially narrower then parts of the flange remote from the leg.

Figure 3B:
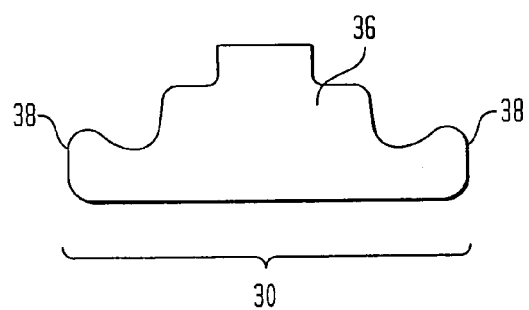
FIG. 3(b) is a rear view of the modified stent flange of FIG. 3(a)

FIG. 3(b) is a rear elevational view showing another embodiment of a flange (36) with upward curling edges (38), so as to form grooves or recesses in its upper area.

Figure 4A:
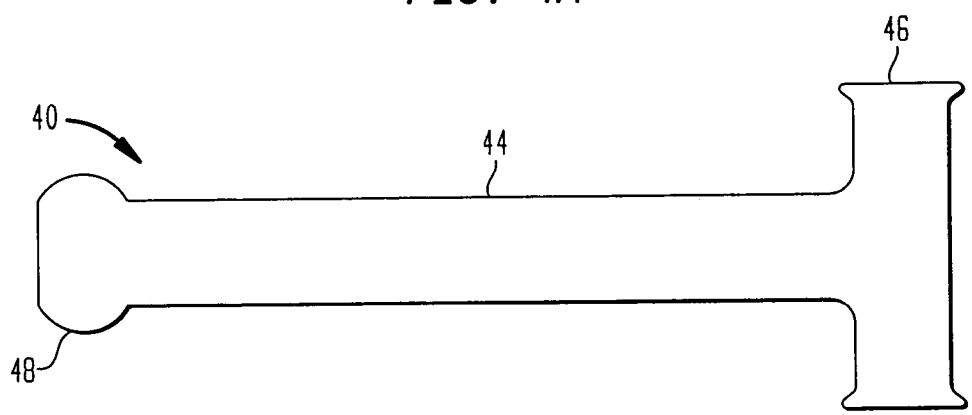
FIGS. 4(a) and 4(b) are respectively top and side views of another embodiment of the scleral stent of the invention.
Figure 4B:
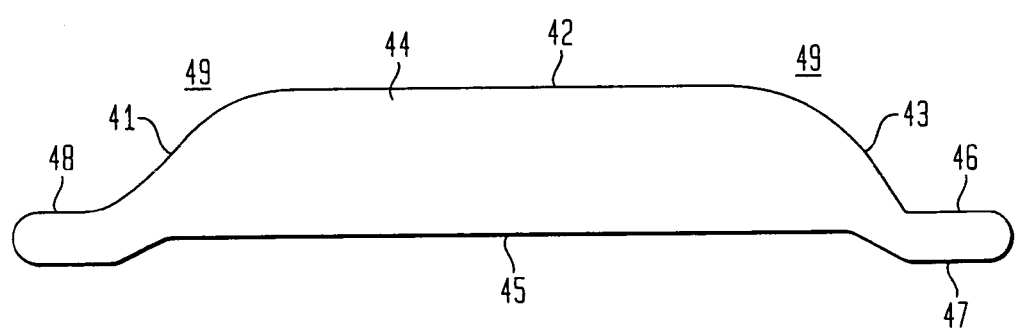

FIG. 4(a) represents a top view of a further embodiment of a scleral stent 40 of the present invention. The leg portion (44) extends between a front region (48) and a torsion-resistant element or flange (46). Similar to the previously described embodiments, the stent (40) comprises a generally T-shaped body having the flange (46) with a rear planar or substantially flat bottom surface (47) and a leg portion (44) extending substantially perpendicularly from a side surface of the flange portion (46). The leg portion (44) is formed at a bottom part thereof with an arcuate region (45) and a substantially flat surface (48) at the front end thereof. As illustrated in FIG. 4 (b), which is a side elevational view of the stent, the leg portion 44 contains a raised or arcuate portion (45) having a curvature or clearance greater than the curvature of the globe in an area of the tunnel. Thus, at least a portion of the arcuate bottom surface is adapted to increase the diameter of the scleral size adjacent the tunnel when the stent is positioned there inside. Furthermore, the near planar or substantially flat surface (47) of the cross portion (46) is designed to be disposed externally to the tunnel for resisting torsional forces on the leg portion.

As illustrated in FIGS. 4 (a) and 4 (b), the torsion-resistant element (46) and the front end of the leg portion (44) are formed having the height substantially smaller than the height of the central area of the stent. The leg portion (44) contains intermediary elements (41) and (43), which connect its top surface (42) with the front end (48) and the torsion-resistant or flange element (46) respectively. As illustrated in FIG. 4 (b), the intermediary portions (41) and (43) are sloped sharply from the maximum height of the leg portion in the central area thereof to a minimum height of the stent at the extremities (48) and (46).

Figure 5A:
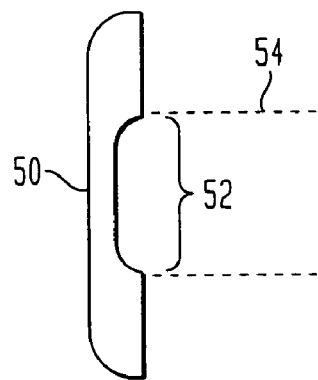
FIGS. 5(a) and 5(b) are respectively top plan and side elevational views of a modified front end portion of the stent showing an anti-torsion element.
Figure 5B:
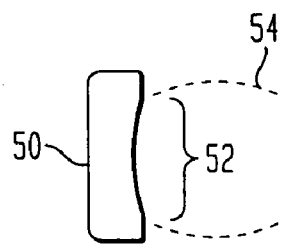
Figure 5C:
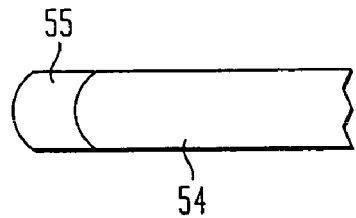
FIGS. 5(c) and 5(d) illustrate an expandable tip arrangement.
Figure 5D:
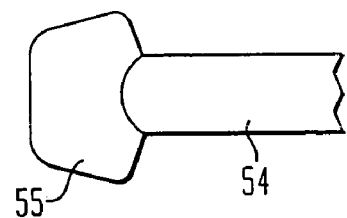

The scleral-tensioning stent of the present invention can be formed with a torsion resistant arrangement other than the above discussed flange or cross-portion. In this respect FIG. 5 (a) illustrates a top-view of an anti-torsion-cap (50) adapted to engage a front end of the stent (54). FIG. 5(b) is a side view of the tapered end anti-torsion-cap (50) of FIG. 5(a). In the assembled condition, a receiving area (52) of the cap engages the front tapered end of the stent (54) (shown in phantom.) The anti-torsion cap (50) can be attached to the tapered end (54) by an adhesive or cement such as amyl acrylate which is typically placed in the receiving area (52).

FIG. 5 (c) and 5 (d) depict a further embodiment of the invention in which a torsion resistant arrangement is in the form of an expandable tip member (55) situated at the front end of the leg (54). As illustrated in FIG. 5(c), in the initial condition, an outer periphery of the tip member (55) coincides with an outer periphery of the front end of the leg (54). Upon insertion of the stent into the tunnel, the tip member (55) expands further securing proper positioning of the stent. The expandable tip (55) can be made of expandable polymer such as hydrating polymer. In an alternative embodiment, the expandable tip (55) can be made in the form of an inflatable member which is inflated upon insertion of the stent (54) into the tunnel.

Expanding biocompatible polymers are known in the art. Reference is made to Isotalo T, Talja M, Tammela T L, Tormala P, Paasimaa S, Andersson L., "Cytotoxicity testing of a new caprolactone-coated self-expanding bioabsorbable self-reinforced poly-L-lactic acid urethral stent." *Urol Res.* 1999 April;27(2):149–52. This publication discloses a urological stent of bioabsorbable self-expanding self-reinforced (SR) poly-L-lactic acid (PLLA) with a coating of an amorphous copolymer of caprolactone and D,L-lactic acid [P(epsilon-CL/D,L-LA)]. Also, Sakkers R J, Dalmeyer R A, de Wijn J R, van Blitterswijk C A, "Use of bone-bonding hydrogel copolymers in bone: An in vitro and in vivo study of expanding PEO-PBT copolymers in goat femora." *J Biomed Mater Res* 2000 March;49(3):312–318. This paper discusses Polyactive(R) [polyethylene oxide-polybuthylene terephtalate (PEO-PBT)] which exhibit hydrogel behavior. And also, Steinberg S D, Mayer D A, Brickman L, Wallack M K, "Regarding: Self-expanding knitted polypropylene mesh facilitates laparoscopic inguinal herniorrhaphy." *J Laparoendosc Adv Surg Tech A* 1999 August;9(4):371–2.

Figure 6A:
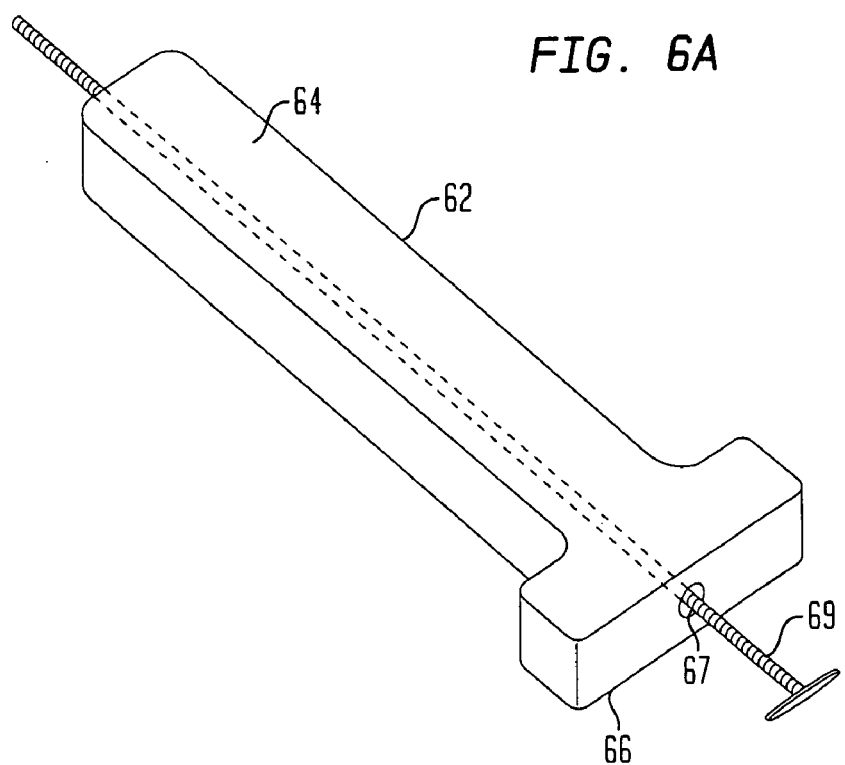
FIG. 6(a) is a semi-perspective view of a further embodiment of a stent made of a resilient material utilizing a removable stylet for maintaining its linear configuration.
Figure 6B:
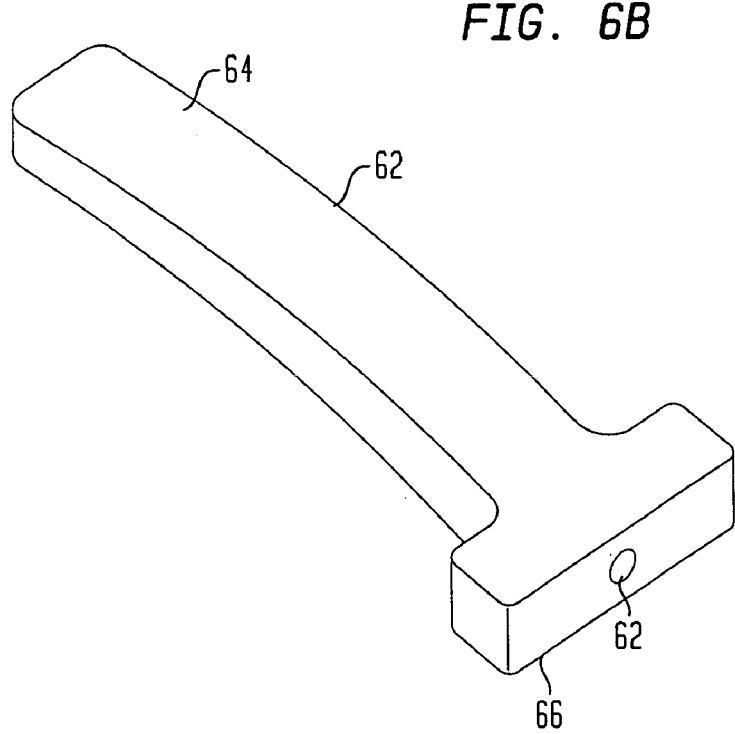
FIG. 6(b) is a semi-perspective view of the stent of FIG. 6(a) with the stylet removed.

FIG. 6(a) is a semi-perspective view of a stent (62) which is similar in configuration to that of FIGS. 1 (a) and 1 (b). The T-shaped scleral-tensioning stent (62) is formed with the leg portion (64) which extends outwardly from the cross-portion or flange (66). As illustrated in FIG. 6 (b), in this embodiment the stent in general and the leg portion thereof (64) in particular are formed having arcuate configuration and can be made of an arcuate-biased material. The main portion or a leg (64) of the stent is connected to the flange (66). The stent (62) is formed with at least one longitudinal bore (67) which passes through its entire length. The linear configuration of the stent is maintained by insertion of a counter-arcuate stylet (69) into the bore (67). The counter-arcuate stylet (69) is typically made of a rigid material such as for example, steel or hard plastic. The counter-arcuate characteristics of the stylet shall mean that the stylet has the rigidity sufficient to maintain a straight-lined configuration of the leg portion of the stent despite the arcuate bias. As illustrated in FIG. 6(b), upon removal of the stylet (69), the stent (64) assumes its original arcuate configuration. It is understood that the stylet can have a variety of cross-sectional shapes such as for example, square, round, etc. Formation of a stent with multiple longitudinal bores adapted for receiving a plurality of counter-arcuate stylets is also contemplated.

Figure 7A:
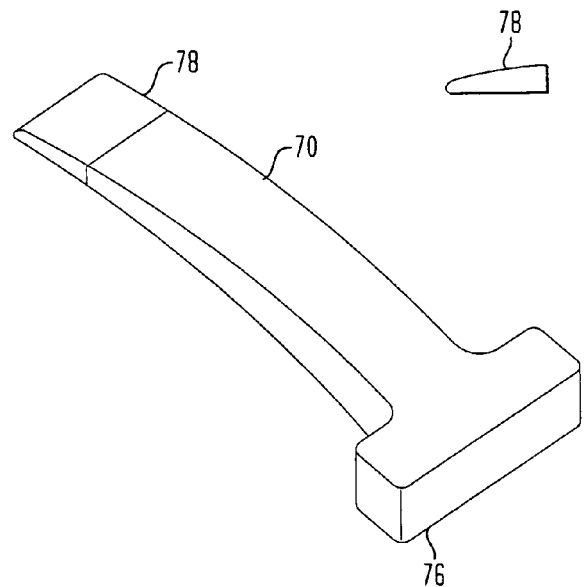
FIG. 7(a) is a view of yet another embodiment of the stent having a blade tip.
Figure 7B:
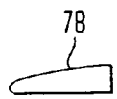
FIG. 7(b) is a side view of the blade tip of FIG. 7(a)
Figure 7C:
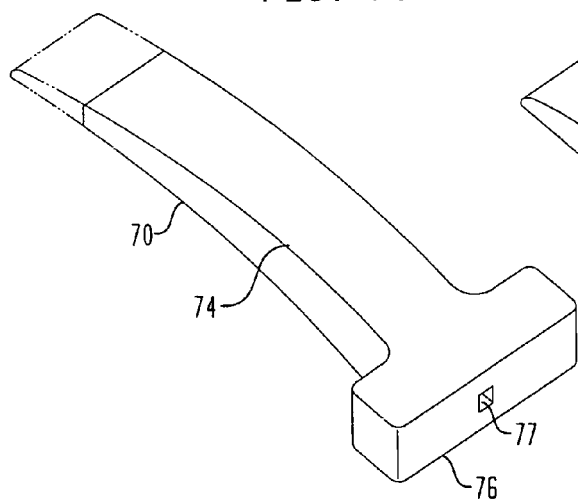
FIG. 7(c) is a semi-perspective view of the stent of FIG. 7(a) showing blade tip in phantom.
Figure 7D:
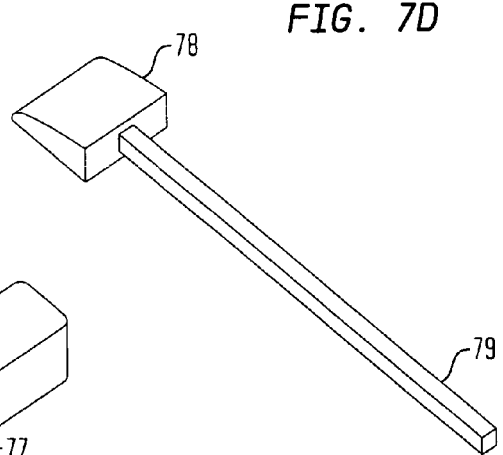
FIG. 7(d) is a semi-perspective view of the blade tip assembly.

FIG. 7(a). illustrates another embodiment of a torsion-resistant stent (70) of the invention having a tapered or wedge-shaped insert blade (78) at the front end thereof.

The insert blade (78) can be made of a hard material suitable for surgical use whether natural or synthetic. Such material can be selected from the group including: diamond, zirconium-like gem stones, and hard steels. The insert blade (78) can be removed from the stent after its positioning within the tunnel.

As illustrated in FIG. 7 (c) a wedge-shaped insert blade (78) is positioned at the front end of the torsion-resistant stent (70). As illustrated in FIG. 7 (d), the wedge-shaped blade assembly consists of the blade (78) and a guiding stylet (79) extending rearwardly therefrom. Proper orientation of the wedge-shaped blade (78) at the front end of the stent (70) is maintained through the insertion of the guiding stylet (79) in the longitudinal bore (77). Although, various configurations of the guiding stylet (79) and the longitudinal bore (77) are contemplated, in the preferred embodiment of the invention, the stylet and the bore are formed having substantially rectangular cross-section. Close engagement of these elements prevents undesirable rotational motion of the wedge-shaped blade assembly relative to the stent.

Upon proper positioning of the stent within the tunnel, the front end of the assembly including the blade (78) extends outwardly therefrom. Then, the blade- and stylet assembly are pulled outwardly and removed from the stent.

FIG. 8. is a semi-perspective view of another embodiment of the scleral stent (82) of the invention. The leg or main portion (84) extends from the torsion-resistant element or flange (86). The scleral stent (82) is formed with a fixation arrangement facilitating placement of sutures (85) about its outer periphery. Although the stent (82) having the fixation arrangement in the form of a single pair of notches is contemplated, in the preferred embodiment of the invention the fixation arrangement contains multiple pairs of notches situated along the length of the leg (84). As illustrated in FIG. 8, one pair of grooves or notches (87) is positioned at a junction between the leg (84) and the flange (86), whereas the other pair of grooves or notches (89) is situated at the front end of the leg portion (84). The sutures (85) are drawn around the stent and run through the underlying sclera and tied or glued in place. Utilization of other types of fixation arrangements such as: clips and staples and the like is also within the scope of the invention.

Figure 12A:
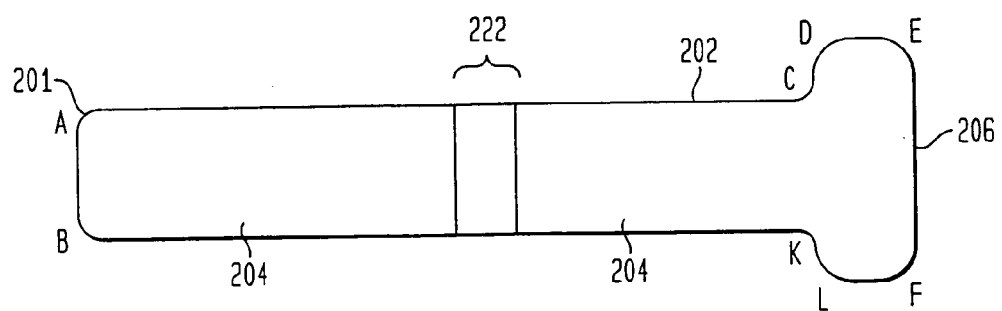
FIG. 12(a) is a top plan view of a further embodiment of the scleral stent of the invention having textured surfaces.
Figure 12B:
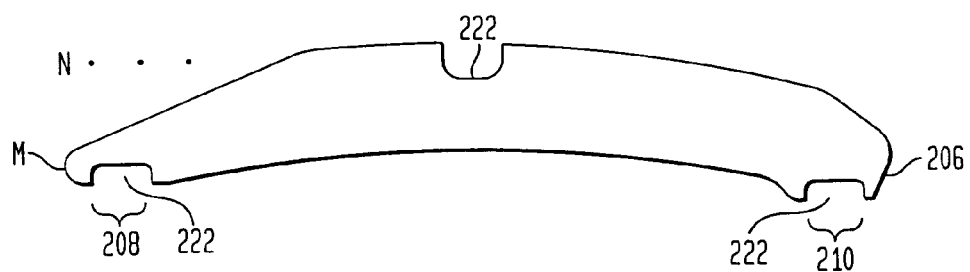
FIG. 12(b) is a side elevational view of the scleral stent of FIG. 12(a)
Figure 12C:
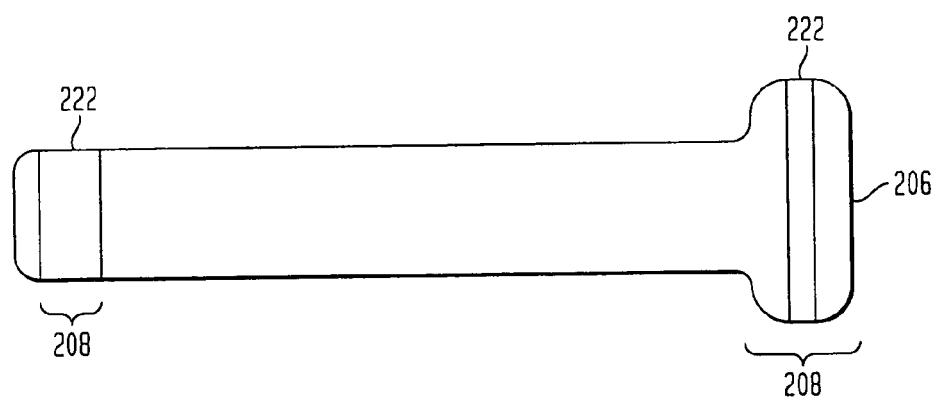
FIG. 12(c) is a bottom plan view of the scleral stent of FIG. 12(a)

FIG. 12(a) represents a top plan view of another embodiment of a scleral stent (202) of the present invention. The leg or main portion (204) of the stent is tapered at the front end (201). The flange (206) is designed to provide torsion-resistance. A tapered portion is formed at the front end of the leg or main portion (204). A flange (206) extends traversely to the main portion. In the embodiment of FIG. 12 (a) the thickness of the stent represented by the segment A-B is about 600 microns. The total length A-E of the stent is about 5 mm. In some embodiments, the length A-E can be about 4.75 mm. The length of each segment A-C and B-K is about 4.5 mm. The length of each segment C-D and K-L is about 250–350 microns, with particular reference to about 300 microns. The length of each segment L-F and D-E is about 500 microns. The length of the segment C-K is between about 600 and 800 microns, with particular reference to about 700 microns. The length of the segment E-F is about 1200 microns. The upper surface of the stent is textured with a groove (222) extending traversely to the direction of the leg or main portion (204). In one embodiment the texture comprises a plurality of grooves about 2/1000 of an inch wide and about 1.5/1000 of an inch deep. Grooves from about 4/1000 to about 0.7/1000 of an inch are particularly noted as useful texturing elements.

Texturing in the form of generally lateral grooving is contemplated using either single or plurality of grooves. Particular note is made to two or more grooves provided at the substantially flat bottom surface of each end of the stent. A stent having grooves formed within side surfaces and/or circumscribing grooves are also contemplated.

To facilitate insertion of the scleral stent (202) into the tunnel during the surgery, the front end is formed with a curved and a tapered portion extending from the front end in the direction of flange (206). Total height of the arched stent (202) is 900 microns shown as M-N based on an 8.8 mm base curve. The length of the torsion-resisting substantially flat surface of the tapered end (208) is about 500 microns. The torsion-resisting flange element (206) is about 500 microns in width (210). The surface is textured with a grooves (222) traversing the width of the torsion resistance elements (206 and 208).

Figure 13A:
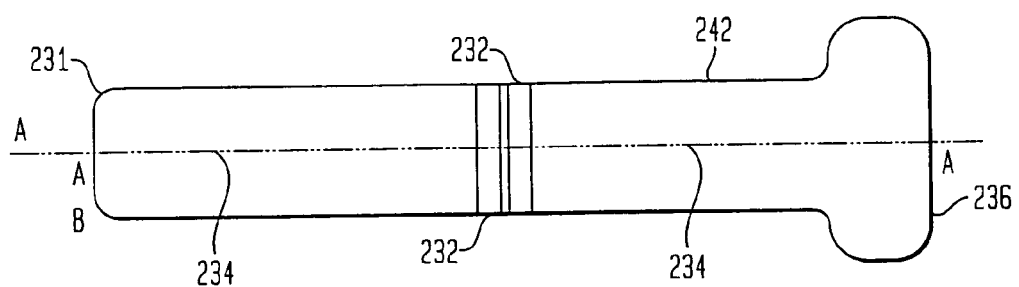
FIG. 13(a) is a top plan view of still another embodiment of the textured scleral stent of the present invention.

FIG. 13(a) represents a top view of a scleral stent (242) of another embodiment of the present invention. The leg or main portion (234) of the stent is tapered at the front end thereof (231). The flange (236) provides torsion-resistance. The top and bottom surfaces of the stent are textured with grooves (232) which are traverse to the direction of the longitudinal axis A—A of the main leg or portion (234).

Figure 13B:
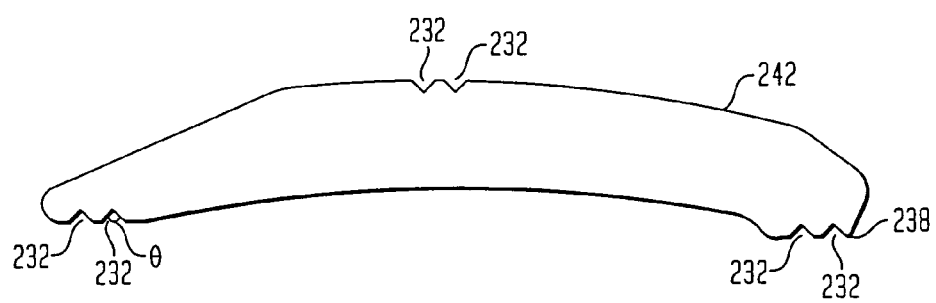
FIG. 13(b) is a side elevational view of the scleral stent of FIG. 13(a)

FIG. 13(b) represents a side elevational view of the scleral stent (242) of FIG. 13(a). The front torsion resistant element (236) and the rear torsion resistant element (238) are formed with a plurality of grooves (232) transversing the longitudinal axis of the stent. The interior angle θ of these grooves is about 90°. In one embodiment the grooves are about 1.5/1000 of an inch wide and about 1/1000 of an inch deep.

Figure 13C:
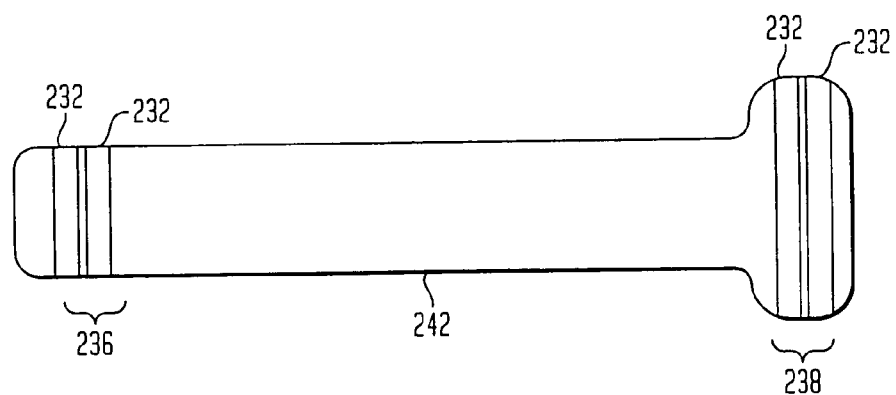
FIG. 13(c) is a bottom view of the scleral stent of FIG. 13(a)

FIG. 13(c) represents a bottom view of the scleral stent (242) of FIG. 13(a) further illustrating the grooves (232) formed within the torsion resistant elements (236 and 238).

Figure 14A:
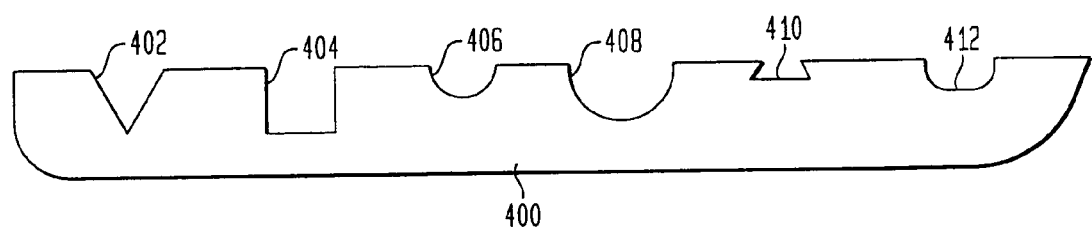
FIG. 14(a) is a view illustrating various textural features of the invention.

FIG. 14(a) illustrates design of various grooves which can be formed within the stent (400). Groove (402) has generally flat walls positioned to each other at an angle to each other of about 60°. Groove (404) are formed with generally flat walls and two base angles of about 90° each. Groove 406 has a semicircular configuration. Groove (408) forms a part of an ellipse. Groove (410) has interior angles of about 60° and represents a groove opening into a space of greater width. Groove 412 is formed by the walls having substantially vertical portions interconnected by an arch-shaped member.

Figure 14B:
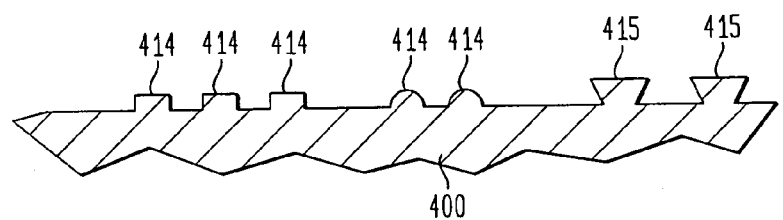
FIG. 14(b) is a view illustrating further stent textures of the invention.

FIG. 14(b) represents a textured surface of stent material with the texture elements (414) being exvaginations ("dentals" or "studs") rather than invaginations. Texture elements (415) are trapezoidal in shape.

Figure 14C:
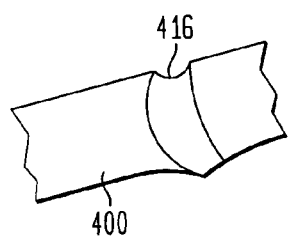
FIG. 14(c) is a view illustrating yet another textural feature of the invention.

FIG. 14(c) is a semi-perspective view of a portion of stent material with the texture element (416) in the form of a circumscribing groove.

Figure 15:
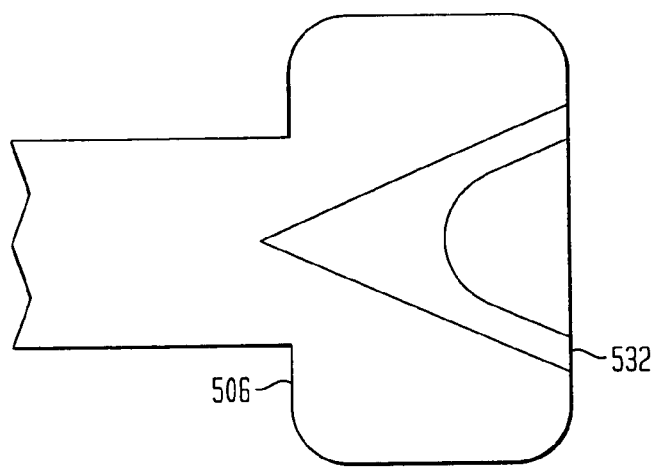
FIG. 15 is a view illustrating a further form of stent texture of the invention.

FIG. 15 is a detailed bottom view of the flange (506) of a stent wherein the texturing is in the form of an arrow shaped groove (532) is provided at the bottom portion thereof. The shape of the groove is directed to permitting inward movement (insertion of a stent) while offering resistance to rearward movement of a stent.

Figure 16:
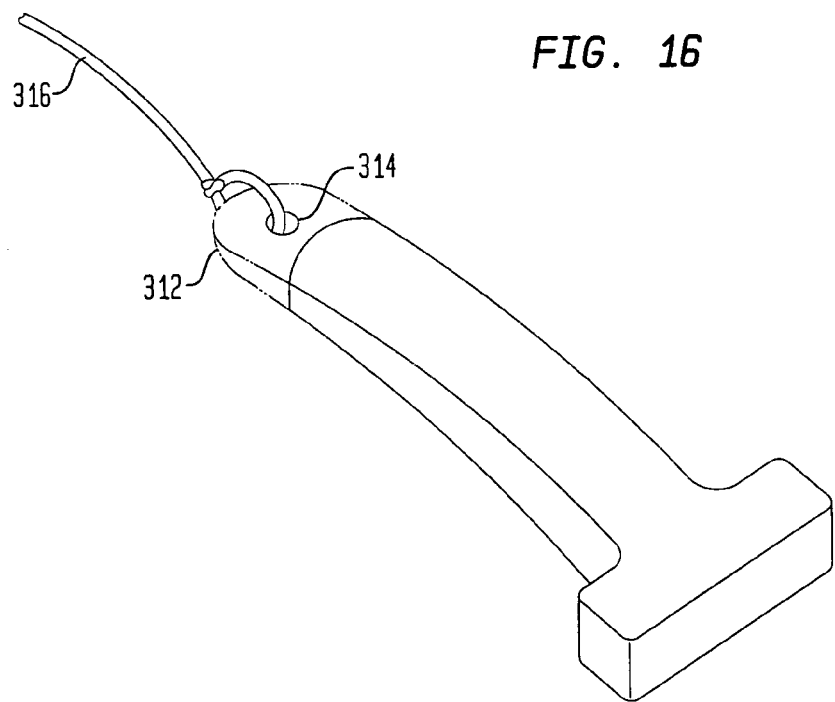
FIG. 16 is a semi-perspective view illustrating a "pull-through" assembly of the invention.

Referring now to FIGS. 16, 16 (a) and 16 (b), wherein a "pull through" device adapted to facilitate a proper positioning of the stent of the invention is within the tunnel is illustrated. A rounded front end (312) of the stent (310) is provided with an attachment opening (314). The attachment opening (314) is designed to receive a pulling arrangement (316), which can be in the form of a cord of a suture material attached to the front end of the stent. In operation, the pulling arrangement (316) can be inserted through the tunnel from either end thereof. The pulling device (316) can be attached to the stent either before or after threading, so as to assist in guiding or pulling the stent into a proper position. In some instances the pulling arrangement is threaded through the sclera in advance of the tunnel being cut or "formed" (as with a laser or cautery tool). After insertion of the stent, the pulling arrangement (316) is removed. In an alternate embodiment, in order to remove the opening (314), the front end portion (312) can be altered by cutting, melting or abrading. The pulling device or member (316) can be manufactured from a great variety of materials including metallic wire and plastic.

Attachment of the pulling arrangement to the front end of the stent by a variety of connecting arrangements is contemplated by the invention. This includes gluing of the pulling member to the front end of the stent, threaded fittings of the member onto the front end of the stent, or one piece construction of an elongated front end of the stent with a thread-like or needle-like projection of stent material being formed at the front end.

Figure 16A:
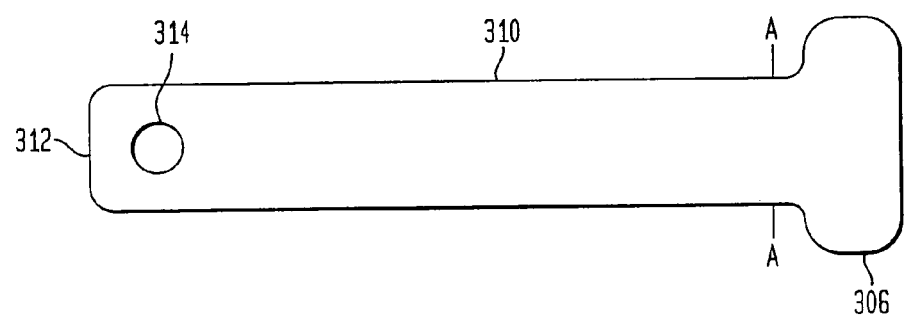
FIG. 16(a) is a top plan view illustrating the stent of the "pull-through" assembly.

As best illustrated in FIG. 16(a) the rounded front end (312) of the stent (310) is formed with an attachment opening (314) The attachment hole is of 0.34 mm in diameter. Dimensionally, the stent is 600 microns wide at the tip bearing attachment hole (314). The stent is 750 microns wide at A—A as it joins the flange element (306). The total length is 4.75 mm. The top is curved from 200 microns in height at the ends to 900 microns at the center of the long axis (apical height).

Figure 16B:
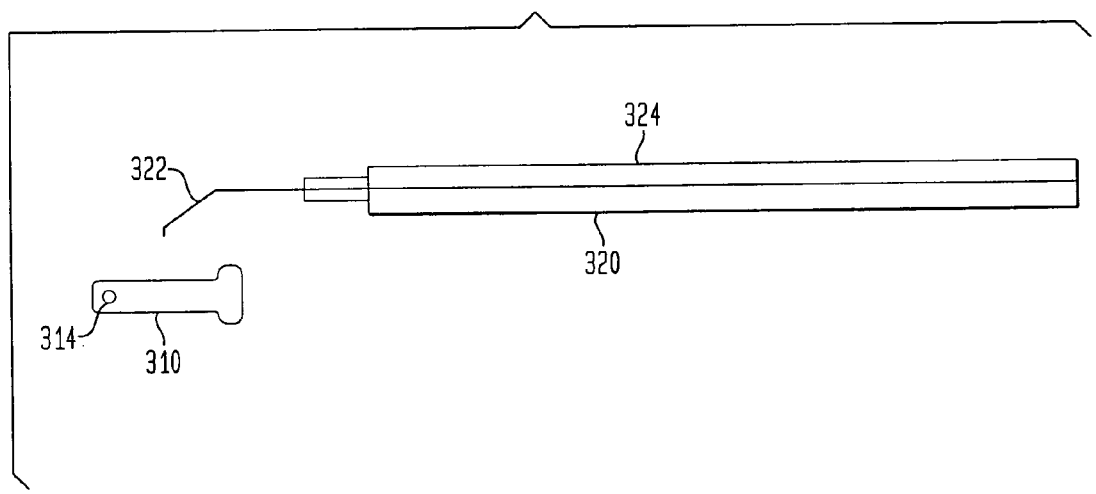
FIG. 16(b) illustrates a stent pulling device.

FIG. 16(b) illustrates the pulling arrangement (320) in the form of a semi-rigid member having a handle (324) and a stent engagement means (322) adapted for engagement with the opening (314). Upon securing of a connection between these element, an operator can draw the stent into the tunnel.

Although the scleral tensioning stent of the invention having a variety of dimensions is contemplated, in the preferred embodiment of the invention the following dimensions are recommended.

In the present embodiment of the invention, the thickness of the stent represented by the segment A-B is about 600 microns. The total length of the stent represented by the segment A-F is about 5 mm. In some embodiments the length A-F is about 4.75 mm. The length of each segment A-K and B-C length is about 4.5 mm. The length of each segment C-D and K-L is about 250–350 microns, with particular reference to about 300 microns. The length of each segment L-F and D-E is about 500 microns. The length of the segment C-K length is about 600 to about 800 microns, with particular reference to about 700 microns. The length of the segment E-F is about 1200 microns.

Figure 1B:
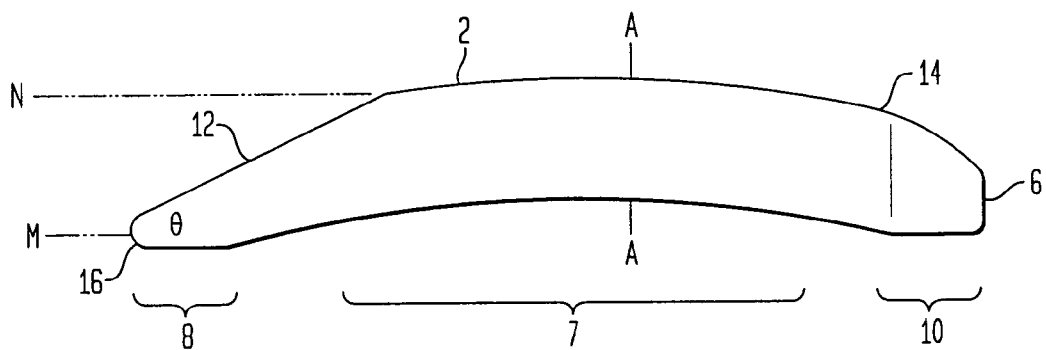
FIG. 1(b) is a side elevational view thereof.

FIG. 1(b) represents a side elevational view of the scleral stent (2) of FIG. 1(a). The total height M-N of the arched stent (2) is about 900 microns based on an 8.8 mm base curve. To facilitate insertion of the stent into the tunnel during surgery, the front tapered region (12) is provided. Taper is noted as angle θ which is from about 25° to about 45°. The length of the front torsion-resistant element or substantially flat bottom surface (8) is about 500 microns. The length of the substantially flat rear bottom surface (10) performing torsion-resistant function is about 500 microns.

Figure 1C:
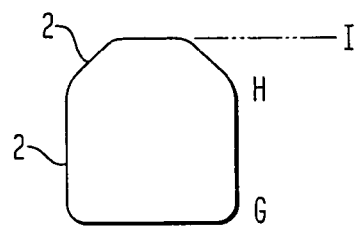
FIG. 1(c) is a section view according to section line A—A of FIG. 1b.

Referring now to FIG. 1(c) which represent a sectional view of the stent according to section line A—A of FIG. 1(b). The height of the segment G-H is about 500 microns, whereas the total height of the segment G-I is from about 700 to about 1000 microns with particular reference to about 900 microns.

Figure 1D:
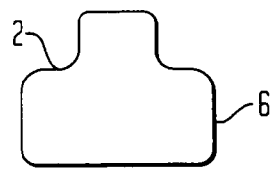
FIG. 1(d) is a rear elevational view of the scleral stent of FIG. 1(a)

As to FIG. 1(d), the width of the torsion-resistant element or flange (6) is about 1200 microns.

Figure 1E:
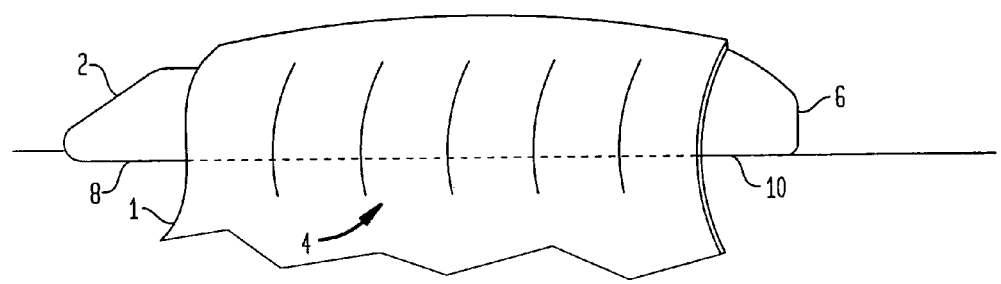
FIG. 1(e) is a semi-perspective view showing a stent protruding from a scleral tunnel.

FIG. 1(e) is a side view of the stent (2) positioned within a tunnel in the sclera (1). The stent in general and the leg portion (4) in particular are situated within the tunnel in such a manner that the front substantially flat surface (8) and the rear substantially flat surface (10) extend outwardly therefrom.

Figure 1F:
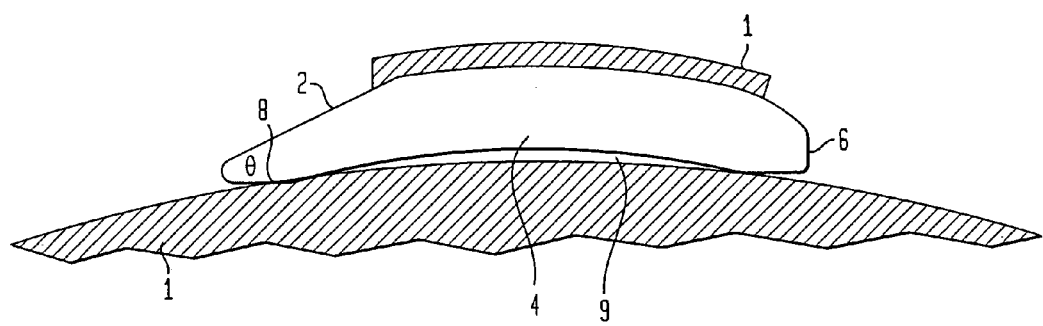
FIG. 1(f) is a side elevation in cutaway showing a stent protruding from a scleral tunnel.

FIG. 1(f) is a side elevation in cutaway showing a stent protruding from a scleral tunnel wherein the stent (2) is positioned within a tunnel in the sclera (1). The stent in general and the leg portion (4) in particular are situated within the tunnel in such a manner that the front substantially flat surface (8) and the rear substantially flat surface (10) extend outwardly therefrom and showing a space (9) between the floor of the scleral tunnel and leg portion (4).

Opacification or clouding of the lens of the eye is termed cataract. Cataracts arise from a number of cause, but is particularly noteworthy as a condition associated with advancing age. Without being bound by any particularly theory it is believed that the increasing immobility and lack of flexion associated with aging lenses permits or fosters cataract. The present invention is useful in delaying preventing the occurrence of cataract formation, particularly as related to increased age. In some instances, stent implants will foster the reversal of cataract and the unclouding of a clouded lens.

Presbyopia Surgical Method

In one embodiment of the surgical procedure such as for presbyopia correction or palliation the first step is to place a drop of 0.5% proparacaine in the eye of a subject being surgically treated. Next, mark the eye at the 12:00 position with the subject seated at a slit lamp, using an 18-gauge sterile needle.

After that, the subject is placed supine upon and the eye is prepped with full strength Povidone-Iodine (Betadine™ Solution). Sterilization preparations which contain soap are not recommended (e.g., Betadine™ Prep). The procedure is performed under monitored local anesthesia. Systemic medications, such as Valium, may be used for relaxation.

A microscope is centered and the eye is draped using a 3M™ 1020 plastic eye drape.

Another drop of 0.5% proparacaine is placed in the eye and a lid speculum is inserted in the conjunctival gutters. The 10:00, 2:00, 4:00 and 8:00 positions are marked, using Gentian Violet or Brilliant Green, using the previously marked 12:00 position as a reference.

Four horizontal incisions of 6 mm are made in the conjunctiva tangential to, and approximately 5–7 mm posterior to, the corneal limbus. If required, bi-polar cautery is used for hemostasis. Dissection is performed down through Tenon's Capsule to the sclera and anteriorly over the sclera to the corneal limbus (clearing the area of sclera to be operated).

Marks are made 2 mm to either side of the previously marked 45-degree meridians (10:00, 2:00, 4:00 and 8:00 positions), to map the entrance and exit of each scleral tunnel. Two partial thickness scleral incisions are made with the Diamond Punch Blade™ in the areas of these marks. The incisions should be about 250–350 microns deep and parallel to each other at a distance of approximately 4-mm, and 2–3 mm posterior to the corneal limbus.

The Spatula Blade™ is used to tunnel between these two partial thickness incisions. The scleral stents are inserted in the tunnels and positioned, making sure that at least about 350 to 500 microns of the stent protrude out each end of the four tunnels. A tweezers that conforms to the shape of the long axis of the stent just ahead of the flange is useful to hold, manipulate and push the stents into the tunnels, and avoid stent twisting or misplacement. In some surgeries, the tunneling blade will be drawn backwards from the point of entry and reinserted into the tunnel being cut. This permits "pocketing" which leads to difficulty in stent insertion. To avoid pockets, if present, the stent should be inserted into the tunnel from a direction opposite to that from which the tunnel was cut. The tapered first portion of the stent (4) A-B is pushed through the tunnel to protrude beyond the slit. Alternatively, the stent is pulled through by the stent pulling device of FIG. 16(b). In practice, a combination of pulling and pushing is used to insert the stent properly. The flanged rear portion (6) of the stent remains outside the tunnel resting on the sclera.

The conjunctiva is re-approximated with 8-0 Chromic or 8-0 Vicryl running suture. One drop of 1% pilocarpine eye drops, and one drop of Tobradex™ eye drops are administered into the conjunctival gutter. About 500 cc of 20% Mannitol are infused intravenously over 30 minutes.

In some embodiments this procedure provides expansion of sclera, non-erosion and no ischemia, and about 2–8 diopters increase in amplitude of accommodation and further up to about 10 diopters increase or more.

In practice, curing or ameliorating the vision deficit such as presbyopia in a single eye is sufficient to satisfy a subject. In such instances, and give that both eyes are of equal deficit, it is prudent to perform the stent implant in the non-dominant eye. If both eyes are to be treated, operating on one eye and then awaiting recovery before operating on the second eye is useful.

Astigmatism is treated by insertion of a stent in the sclera in a "tunnel" in a fashion similar to the presbyopia placement. Except that for astigmatism, placement is, in some embodiments, nearer the lens but not in the visual path than is the case with presbyopia treatment. Also, one to three stents are often sufficient. Placement of the stents is made to raise the outer surface of the lens in from one to three visual quadrants. It is preferred to avoid placing stents at 12, 3, 6 and 9:00 positions to avoid compression of the underlying vasculature. In some embodiments, placement, and then removal and reinsertion of stents after the site of initial insertion has healed is required to reduce astigmatism. The reinsertion is then performed at slightly different positions (advancing clockwise or counter clockwise) to "tune" the lens perturbation to maximally reduce the underlying lens anomaly that was the cause of the presenting astigmatism.

What is claimed is:

1. A torsion resistant scleral-tensioning stent for positioning in a tunnel formed intrasclerally in a globe of an eye, comprising:
   a generally t-shaped body having a cross portion with a top surface, a bottom surface and a leg portion extending substantially perpendicularly from a side surface of said cross portion;
   said leg portion having a top surface, a bottom surface with an arcuate portion and a substantially planar portion at an end of said leg portion distal from said cross portion;
   wherein said arcuate portion has a radius of curvature from about 8 mm to about 9 mm;
   wherein said top surfaces of said cross portion and said leg portion define a t-shaped configuration; and
   wherein said bottom surface of said cross portion is dimensioned to be disposed external to said tunnel for resisting torsional forces on said leg portion.

2. The stent of claim 1 wherein said cross portion extends beyond said tunnel.

3. The stent of claim 1 wherein is said stent is out-gassing free.

4. The stent of claim 3 comprising thermosetting PMMA.

5. The stent of claim 1 wherein said stent is arcuate biased.

6. The stent of claim 1 wherein the cross portion is flat on the bottom surface.

7. The stent of claim 1 wherein the distal end of the stent is tapered.

8. The stent of claim 1, wherein the top surface of the leg portion is narrower than the bottom surface of the leg portion.

9. A scleral-tensioning stent for positioning in a tunnel formed intrasclerally in a globe of an eye, comprising:
   an elongated portion having a top surface and a bottom surface, the bottom surface forming an arc along a portion of a length of the elongated portion;
   a flange, integrally formed with and at a first distal end of the elongated portion and oriented perpendicularly to the elongated portion, having a top surface, a bottom surface and a length wider than a width of the first end of the elongated portion; the flange is flat on the bottom surface;
   wherein the bottom surface of a second end of the elongated portion, opposite the first distal end, forms a flat surface; and
   wherein said top surfaces of said elongated portion and said flange define a t-shaped configuration.

10. The stent of claim 9, wherein the arc is of a smaller radius than a radius of the globe of the eye proximate to the tunnel.

11. The stent of claim 9, wherein the arc ends at the first distal end of the elongated portion at the flange.

12. The stent of claim 9, wherein the top surface of the elongated portion is narrower than the bottom surface of the elongated portion.

13. The stent of claim 9, wherein the elongated portion is arcuate along its length.

14. The stent of claim 9, wherein the arc has a radius of about 8 to about 9 mm.

15. A torsion resistant scleral-tensioning stent for positioning in a tunnel formed intrasclerally in a globe of an eye, comprising:
   a generally capital t-shaped body having a cross portion with a top surface, a flat bottom surface and a leg portion extending substantially perpendicularly from a side surface of said cross portion;
   said leg portion having a top surface, a bottom surface with an arcuate portion and a substantially planar portion at an end of said leg portion distal from said cross portion;
   wherein said top surfaces of said cross portion and said leg portion define a t-shaped configuration; and
   wherein said bottom surface of said cross portion is dimensioned to be disposed external to said tunnel for resisting torsional forces on said leg portion.

16. A scleral-tensioning stent for positioning in a tunnel formed intrasclerally in a globe of an eye, comprising:
   an elongated portion having a top surface and a bottom surface, the bottom surface forming an arc along a portion of a length of the elongated portion;
   a flange, integrally formed with and at a first end of the elongated portion and oriented perpendicularly to the elongated portion, having a top surface, a bottom surface and a length wider than a width of the first end of the elongated portion to form the shape of a capital T;
   wherein said top surfaces of said elongated portion and said flange define a t-shaped configuration; and
   wherein the top surface of the elongated portion is narrower than the bottom surface of the elongated portion.

* * * * *

(12) EX PARTE REEXAMINATION CERTIFICATE (8220th)
United States Patent
Straub

(10) Number: US 7,008,396 C1
(45) Certificate Issued: May 10, 2011

(54) OPHTHALMIC DEVICE AND METHOD OF MANUFACTURE AND USE

(75) Inventor: Howard N. Straub, Aurora, CO (US)

(73) Assignee: Restorvision, Inc., Greenwood Village, CO (US)

Reexamination Request:
No. 90/008,202, Aug. 30, 2006
No. 90/008,315, Nov. 3, 2006

Reexamination Certificate for:
Patent No.: 7,008,396
Issued: Mar. 7, 2006
Appl. No.: 09/650,584
Filed: Aug. 30, 2000

Related U.S. Application Data

(60) Provisional application No. 60/152,455, filed on Sep. 3, 1999, provisional application No. 60/178,395, filed on Jan. 27, 2000, and provisional application No. 60/206,134, filed on May 22, 2000.

(51) Int. Cl.
*A61M 27/00* (2006.01)
*A61M 5/00* (2006.01)

(52) U.S. Cl. .......................................................... 604/8
(58) Field of Classification Search ....................... 604/8
See application file for complete search history.

(56) References Cited

U.S. PATENT DOCUMENTS

| 5,879,319 A | * | 3/1999 | Pynson et al. | 604/8 |
| 6,280,468 B1 | | 8/2001 | Schachar | 623/4.1 |
| 2005/0283233 A1 | | 12/2005 | Schachar | 623/4.1 |

FOREIGN PATENT DOCUMENTS

FR 2784287 A1 * 4/2000

* cited by examiner

*Primary Examiner*—Aaron J. Lewis

(57) ABSTRACT

A torsion resistant scleral-tensioning stent useful in the correction of presbyopia and further including a method of chronic ocular fluid control utilizing such device.

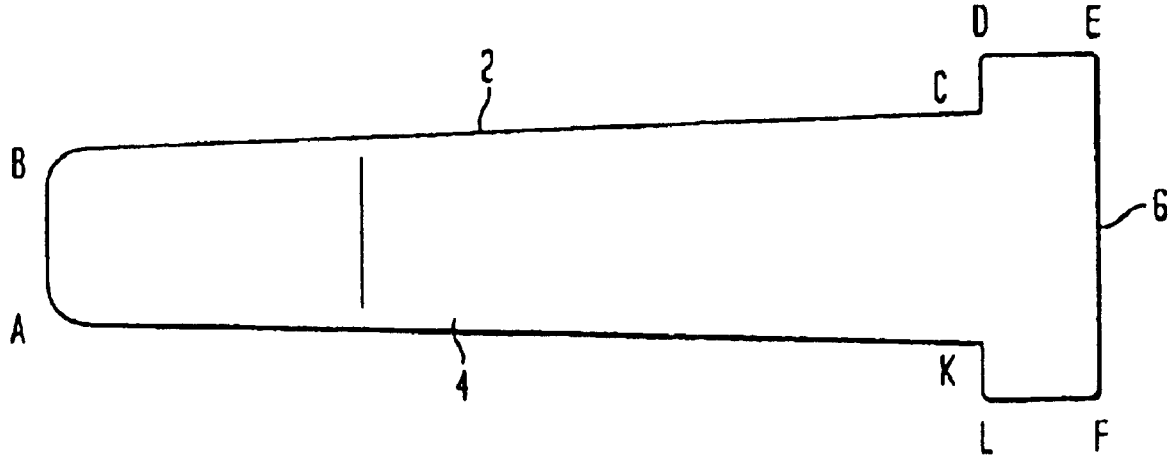

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-16 is confirmed.

* * * * *